(12) United States Patent
Cardone

(10) Patent No.: US 9,360,473 B2
(45) Date of Patent: Jun. 7, 2016

(54) ASSAY SYSTEM TO IDENTIFY THERAPEUTIC AGENTS

(75) Inventor: Michael H. Cardone, Dorchester, MA (US)

(73) Assignee: EUTROPICS PHARMACEUTICALS, INC., Cambridge, MA (US)

(*) Notice: Subject to any disclaimer, the term of this patent is extended or adjusted under 35 U.S.C. 154(b) by 1856 days.

(21) Appl. No.: 12/377,746

(22) PCT Filed: Aug. 16, 2007

(86) PCT No.: PCT/US2007/018238
§ 371 (c)(1),
(2), (4) Date: Jan. 25, 2011

(87) PCT Pub. No.: WO2008/021484
PCT Pub. Date: Feb. 21, 2008

(65) Prior Publication Data
US 2011/0130309 A1    Jun. 2, 2011

Related U.S. Application Data

(60) Provisional application No. 60/838,284, filed on Aug. 16, 2006.

(51) Int. Cl.
| C40B 40/10 | (2006.01) |
| G01N 33/50 | (2006.01) |
| G01N 33/53 | (2006.01) |
| G01N 33/574 | (2006.01) |
| A61K 49/00 | (2006.01) |

(Continued)

(52) U.S. Cl.
CPC ........ *G01N 33/5079* (2013.01); *A61K 49/0004* (2013.01); *C40B 40/10* (2013.01); *G01N 33/586* (2013.01); *G01N 33/53* (2013.01); *G01N 33/543* (2013.01); *G01N 33/574* (2013.01); *G01N 2510/00* (2013.01)

(58) Field of Classification Search
None
See application file for complete search history.

(56) References Cited

U.S. PATENT DOCUMENTS

| 5,674,980 A | 10/1997 | Frankel et al. |
| 5,804,604 A | 9/1998 | Frankel et al. |

(Continued)

FOREIGN PATENT DOCUMENTS

| WO | WO 97/05265 | 2/1997 |
| WO | WO 00/06187 | 2/2000 |

(Continued)

OTHER PUBLICATIONS

Gross et al., "BCL-2 family members and the mitochondria in apoptosis," Genes Dev. 1999, 13:1899-1911.*

(Continued)

*Primary Examiner* — Samuel Woolwine
*Assistant Examiner* — Kaijiang Zhang
(74) *Attorney, Agent, or Firm* — Cooley LLP

(57) ABSTRACT

The invention is an assay designed to identify agents that modulate apoptosis. The invention provides an assay system and methods for screening for inhibitors of the Bcl-2 family of proteins. In various aspects the invention provides an assay system containing a liposome reagent and an immobilized BH3 domain peptide. In further aspects the invention provides an assay system containing mitochondria, an immobilized BH3 domain peptide and a mitochondrial binding agent, e.g. an anti-VDAC anti-body.

8 Claims, 4 Drawing Sheets

(51) Int. Cl.
  G01N 33/58 (2006.01)
  G01N 33/543 (2006.01)

(56) References Cited

U.S. PATENT DOCUMENTS

| | | | |
|---|---|---|---|
| 6,022,720 A | | 2/2000 | Martinou |
| 2002/0076727 A1* | | 6/2002 | Cardone et al. ............... 435/7.1 |
| 2008/0199890 A1* | | 8/2008 | Letai ............................ 435/7.23 |
| 2008/0274962 A1* | | 11/2008 | Shoshan-Barmatz et al. .. 514/12 |
| 2010/0221709 A1* | | 9/2010 | Hockenbery et al. ............ 435/6 |

FOREIGN PATENT DOCUMENTS

| WO | WO 2004/022580 A2 | 3/2004 |
|---|---|---|
| WO | WO 2004/058804 A1 | 7/2004 |

OTHER PUBLICATIONS

Hutter et al., "Senescence-associated changes in respiration and oxidative phosphorylation in primary human fibroblasts," Biochem. J. 2004, 380:919-928.*
Min et al., "Peptide arrays: towards routine implementation," Curr. Opin. Chem. Biol. 2004, 8:554-558.*
Gaus et al., "Assessment of the fifth ligand-binding repeat (LR5) of the LDL receptor as an analytical reagent for LDL binding," Analyst 2001, 126:329-336.*
M. Certo, V. Del Gaizo Moore, M. Nishino, G. Wei, S. Korsmeyer, S.A. Armstrong, and A. Letai, "Mitochondria Primed by Death Signals Determine Cellular Addiction to Antiapoptotic BCL-2 Family Members," Cancer Cell 9:351-365 (May 2006). 2006 Elsevier Inc.
J. Deng, N. Carlson, K. Takeyama, P. Dal Cin, M. Shipp, and A. Letai, "BH3 Profiling Identifies Three Distinct Classes of Apoptotic Blocks to Predict Response to ABT-737 and Conventional Chemotherapeutic Agents," Cancer Cell 12:171-185 (Aug. 2007), 2007 Elsevier Inc.
D. Green, "Life, Death, BH3 Profiles, and the Salmon Mousse," Cancer Cell 12:97-99 (Aug. 2007) 2007 Elsevier Inc.
S.M. Fuchs and R.T. Raines; "Pathway for Polyarginine Entry into Mammalian Cells," Biochemistry 43(9): 2438-44 (Mar. 2004) 2004 American Chemical Society.
S.N. Willis, J.I. Fletcher, T. Kaufmann, M.F. van Delft, L. Chen, P.E. Czabotar, H. Ierino, E.F. Lee, W.D. Fairlie, P.Bouillet, A. Strasser, R.M. Kluck, J.M. Adams, D.C. S. Huang, "Apoptosis Initiated When BH3 Ligands Engage Multiple Bcl-2 Homologs, not Bax or Bak," Science 315:856-59 (Feb. 2007) 2007 American Association for the Advancement of Science.
P.E. Czabotar, P.M. Colman, and D.C.S. Huang, "Bax Activation by Bim?," Cell Death and Differentiation 16:1187-91 (Sep. 2009). 2009 Macmillan Publishers Limited.
S.J. Martin, "Opening the Cellular Poison Cabinet," Science 330:1330-1331 (Dec. 2010) 2010 American Association for the Advancement of Science.
D. Ren, H. Tu, H. Kim, G.X. Wang, G.R. Bean, O.Takeuchi, J.R. Jeffers, G.P. Zambetti, J.J.-D. Hsieh, E.H.-Y. Cheng, "BID, BIM, and PUMA Are Essential for Activation of the BAX- and BAK-Dependent Cell Death Program," Science 330:1390-93 (Dec. 2010) 2010 American Association for the Advancement of Science.
O. Gul, H. Basaga and O. Kutuk, "Apoptotic blocks and chemotherapy resistance: strategies to identify Bcl-2 protein signatures," (Jan. 2008) Briefings in Functional Genomics and Proteomics 7(1):27-34 2008 Oxford University Press.
W. Strupp, G. Weidinger, C. Scheller, R. Ehret, H. Ohnimus, H. Girschick, P. Tas, E. Flory, M. Heinkelein and C. Jassoy, "Treatment of Cells with Detergent Activates Caspases and Induces Apoptotic Cell Death," (Jun. 2000) J. Membrane Biology 175 (3): 181-189 2000 Springer.
Brady et al., "Reflections on a peptide", Nature, 368:692-693 (1994).
DeGrado, W.R., in Advances in Protein Chemistry, 39:51-124 (1988).
Jameson et al., "A rationally designed CD4 analogue inhibits experimental allergic encephalomyelitis", Nature, 368:744-746 (1994).

Samson et al., "A 35 amino acid fragment of leptin inhibits feeding in the rat", Endocrinology, 137(11):5182-5185 (1996).
Adams et al., "The Bcl-2 Protein Family: Arbiters of Cell Survival", Science, 281(5381):1322-1326 (1998).
Bae et al., "Underphosphorylated BAD interacts with diverse antiapoptotic Bcl-2 family proteins to regulate apoptosis", Apoptosis, 6:319-330 (2001).
Bouillet et al., "Proapoptotic Bcl-2 Relative Bim Required for Certain Apoptotic Responses, Leukocyte Homeostatis, and to Preclude Autoimmunity", Science, 286:1735-1738 (1999).
Boyd et al., "Bik, a novel death-inducing protein shares a distinct sequence motif with Bcl-2 family proteins and interacts with viral and cellular survival-promoting proteins", Oncogene, 11:1921-1928 (1995).
Calin et al., "A MicroRNA Signature Associated with Prognosis and Progression in Chronic Lymphocytic Leukemia", N. Engl. J. Med., 353:1793-1801 (2005).
Cartron et al., "The first α Helix of Bax Play a Necessary Role in Its Ligand-Induced Activation by the BH3-Only Proteins Bid and PUMA", Mol. Cell, 16:807-818 (2004).
Chen et al., "Caspase cleavage of $Bim_{EL}$ triggers a positive feedback amplification of apoptotic signaling", Proc. Natl. Acad. Sci. USA, 101(5):1235-1240 (2004).
Chen et al., "Differential Targeting of Prosurvival Bcl-2 Proteins by Their BH3-Only Ligands Allows Complementary Apoptotic Function", Mol. Cell, 17:393-403 (2005).
Cheng et al., "Bax-independent inhibition of apoptosis by $Bcl-x_L$", Nature, 379:554-556 (1996).
Cheng et al., "BCL-2, $BCL-X_L$ Sequester BH3 Domain-Only Molecules Preventing BAX- and BAK-Mediated Mitochondrial Apoptosis", Mol. Cell, 8:705-711 (2001).
Chipuk et al., "Direct Activation of Bax by p53 Mediates Mitochondrial Membrane Permeabilization and Apoptosis", Science, 303:1010-1014 (2004).
Chittenden et al., "A conserved domain in Bak, distinct form BH1 and BH2, mediates cell death and protein binding functions", EMBO J., 14(22):5589-5596 (1995).
Chittenden et al., "Induction of apoptosis by the Bcl-2 homologue Bak", Nature, 374(6524):733-736 (1995).
Cory et al., "The Bcl2 Family: Regulators of the Cellular Life-Or-Death Switch", Nat. Rev. Cancer, 2(9):647-656 (2002).
Danial et al., "Cell Death: Critical Control Points", Cell, 116:205-219 (2004).
Derenne et al., "Antisense strategy shows that Mcl-1 rather than Bcl-2 or $Bcl-x_L$ is an essential survival protein of human myeloma cells", Blood, 100: 194-199 (2002).
Desagher et al., "Bid-induced Conformational Change of Bax Is Responsible for Mitochondrial Cytochrome c Release during Apoptosis", J. Cell Biol., 144(5):891-901 (1999).
Di Lisa et al., "Mitochondrial Function and Cell Injury in Single Cardiac Myocytes Exposed to Anoxia and Reoxygenation", Transplant. Proc., 27(5):2829-2830 (1995).
Di Lisa et al., "Mitochondrial membrane potential in single living adult rat cardiac myocytes exposed to anoxia or metabolic inhibition", J. Physiol., 486(1):1-13 (1995).
Dohner et al., "Genomic Aberrations and Survival in Chronic Lymphocytic Leukemia", N. Engl. J. Med., 343:1910-1916 (2000).
Egle et al., "Bim is a suppressor of Myc-induced mouse B cell leukemia", Proc. Natl. Acad. Sci. USA, 101(16):6164-6169 (2004).
Elliott et al., "Intercellular Trafficking and Protein Delivery by a Herpesvirus Structural Protein", Cell, 88:223-233 (1997).
Eskes et al., "Bid Induces the Oligomerization and Insertion of Bax into the Outer Mitochondrial Membrane", Mol. Cell. Biol., 20(3):929-935 (2000).
Fanidi et al., "Cooperative interaction between c-myc and bcl-2 proto-oncogenes", Nature, 359:554-556 (1992).
Frankel et al., "Activity of synthetic peptides from the Tat protein of human immunodeficiency virus type 1", Proc. Natl. Acad. Sci. USA, 86:7397-7401 (1989).
Green et al., "A matter of life and death", Cancer Cell, 1:19-30 (2002).
Green et al., "The Pathophysiology of Mitochondrial Cell Death", Science, 305:626-629 (2004).

(56) References Cited

OTHER PUBLICATIONS

Griffiths et al., "Cell Damage-induced Conformational Changes of the Pro-Apoptotic Protein Bak In Vivo Precede the Onset of Apoptosis", *J. Cell Biol.*, 144(5):903-914 (1999).
Gross et al., "Enforced dimerization of BAX results in its translocation, mitochondrial dysfunction and apoptosis", *EMBO J.*, 17(14):3878-3885 (1998).
Hanahan et al., "The Hallmarks of Cancer", *Cell*, 100:57-70 (2000).
Harada et al., "Survival factor-induced extracellular signal-regulated kinase phosphorylates BIM, inhibiting its association with BAX and proapoptotic activity", *Proc. Natl. Acad. Sci. USA*, 101(43):15313-15317 (2004).
Hemann et al., "Evasion of the p53 tumour surveillance network by tumour-derived MYC mutants", *Nature*, 436:807-811 (2005).
Hemann et al., "Suppression of tumorigenesis by the p53 target PUMA", *Proc. Natl. Acad. Sci. USA*, 101(25):9333-9338 (2004).
Hengartner et al., "C. elegans Cell Survival Gene ced-9 Encodes a Functional Homolog of the Mammalian Proto-Oncogene *bcl-2*", *Cell*, 76:665-676 (1994).
Holinger et al., "Bak BH3 Peptides Antagonize Bcl-$x_L$ Function and Induce Apoptosis through Cytochrome c-independent Activation of Caspases", *J. Biol. Chem.*, 274(19):13298-13304 (1999).
Hsu et al., "Nonionic Detergents Induce Dimerization among Members of the Bcl-2 Family", *J. Biol. Chem.*, 272(21):13829-13834 (1997).
Huang et al., "BH3-Only Proteins—Essential Initiators of Apoptotic Cell Death", *Cell*, 103:839-842 (2000).
Inohara et al., "*harakiri*, a novel regulator of cell death, encodes a protein that activates apoptosis and interacts selectively with survival-promoting proteins Bcl-2 and Bcl-$X_L$", *Embo J.*, 16(7):1686-1694 (1997).
Jackson et al., "Heat shock induces the release of fibroblast growth factor 1 from NIH 3T3 cells", *Proc. Natl. Acad. Sci. USA*, 89:10691-10695 (1992).
Jonkers et al., "Oncogene addiction: Sometimes a temporary slavery", *Cancer Cell*, 6:535-538 (2004).
Kelekar et al., "Bad is a BH3 Domain-Containing Protein that Forms an Inactivating Dimer with Bcl-$x_L$"• *Mol. Cell Biol.*, 17(12):7040-7046 (1997).
Kelekar et al., "Bcl-2-family proteins: the role of the BH3 domain in apoptosis", *Trends Cell Biol.*, 8:324-330 (1998).
Kuwana et al., "BH3 Domains of BH3-Only Proteins Differentially Regulate Bax-Mediated Mitochondrial Membrane Permeabilization Both Directly and Indirectly." *Mol. Cell*, 17:525-535 (2005).
Kuwana et al., "Bid, Bax, and Lipids Cooperate to Form Supramolecular Openings in the Outer Mitochondrial Membrane", *Cell*, 111:331-342 (2002).
Leo et al., "Characterization of the Antiapoptotic Bcl-2 Family Member Myeloid Cell Leukemia-1 (Mcl-1) and the Stimulation of Its Message by Gonadotropins in the Rat Ovary", *Endocrinol.*, 140(12):5469-5477 (1999).
Letai et al., "Antiapoptotic BCL-2 is required for maintenance of a model leukemia", *Cancer Cell*, 6:241-249 (2004).
Letai et al., "Distinct BH3 domains either sensitize or activate mitochondrial apoptosis, serving as prototype cancer therapeutics", *Cancer Cell*, 2:183-192 (2002).
Letai, A., "BH3 domains in BCL-2 inhibitors: prototype cancer therapeutics", *Exp. Opin. Biol. Ther.*, 3(2):293-304 (2003).
Letai, A., "The BCL-2 network: Mechanistic insights and therapeutic potential", *Drug Disc. Today: Disease Mechanisms*, 2(2):145-151 (2005).
Liu et al., "Bax conformational change is a crucial step for PUMA-mediated apoptosis in human leukemia", *Biochem. Biophys. Res. Commun.*, 310(3):956-962 (2003).
Luo et al., "Bid, a Bcl2 Interacting Protein, Mediates Cytochrome c Release from Mitochondria in Response to Activation of Cell Surface Death Receptors", *Cell*, 94:481-490 (1998).
Marani et al., "Identification of Novel Isoforms of the BH3 Domain Protein Bim which Directly Activate Bax to Trigger Apoptosis", *Mol. Cell. Biol.*, 22(11):3577-3589 (2002).

McDonnell et al., "*bcl*-2-Immunoglobulin Transgenic Mice Demonstrate Extended B Cell Survival and Follicular Lymphoproliferation", *Cell*, 57:79-88 (1989).
Means et al., "Modifications to change properties", in *Chemical Modification of Protein*, Chapter 3, pp. 35-54, Holden-Day (1974).
Muchmore et al., "X-ray and NMR structure of human Bcl-$x_L$, an inhibitor of programmed cell death", *Nature*, 381:335-341 (1996).
Nakano et al., "PUMA, a Novel Proapoptotic Gene, is Induced by p53", *Mol. Cell*, 7:683-694 (2001).
O'Brien et al., "Phase I and II Multicenter Study of Oblimersen Sodium, a Bcl-2 Antisense Oligonucleotide, in Patients With Advanced Chronic Lymphocytic Leukemia", *J. Clin. Oncol.*, 23(30):7697-7702 (2005).
O'Connor et al., "Bim: a novel member of the Bcl-2 family that promotes apoptosis", *Embo J.*, 17(2):384-395 (1998).
Oda et al., "Noxa, a BH3-Only Member of the Bcl-2 Family and Candidate Mediator of p53-Induced Apoptosis", *Science*, 288:1053-1058 (2000).
Oh et al., "Conformational Changes in BID, a Pro-apoptotic BCL-2 Family Member, upon Membrane Binding", *J. Biol. Chem.*, 280(1):753-767 (2005).
Oltersdorf et al., "An inhibitor of Bcl-2 family proteins induces regression of solid tumours", *Nature*, 435:677-681 (2005).
Opferman et al., "Development and maintenance of B and T lymphocytes requires antiapoptotic MCL-1", *Nature*, 426:671-676 (2003).
Puthalakath et al., "Bmf: a Proapoptotic BH3-Only Protein Regulated by Interaction with the Myosin V Actin Motor Complex, Activated by Anoikis", *Science*, 293:1829-1832 (2001).
Puthalakath et al., "Keeping killers on a tight leash: transcriptional and post-translational control of the pro-apoptotic activity of BH3-only proteins", *Cell Death Differ.*, 9:505-512 (2002).
Puthalakath et al., "The Proapoptotic Activity of the Bcl-2 Family Member Bim is Regulated by Interaction with the Dynein Motor Complex", *Mol. Cell*, 3:287-296 (1999).
Raff, M.C., "Social controls on cell survival and cell death", *Nature*, 356(6368):397-400 (1992).
Rassenti et al., "ZAP-70 Compared with Immunoglobulin Heavy-Chain Gene Mutation Status as a predictor of Disease Progression in Chronic Lymphocytic Leukemia", *N. Engl. J. Med.*, 351:893-901 (2004).
Ray et al., "BNIP3 Heterodimerizes with Bcl-2/Bcl-$X_L$ and Induces Cell Death Independent of a Bcl-2 Homology 3 (BH3) Domain at Both Mitochondrial and Nonrnitochondrial Sites", *J. Biol. Chem.*, 275(2): 1439-1448 (2000).
Sattler et al., "Structure of Bcl-$x_L$-Bak Peptide Complex: Recognition Between Regulators of Apoptosis", *Science*, 275:983-986 (1997).
Vaux et al., "*Bcl-2* gene promotes haemopoietic cell survival and cooperates with *c-myc* to immortalize pre-B cells", *Nature*, 335(6189):440-442 (1988).
Vives et al., "A Truncated HIV-1 Tat Protein Basic Domain Rapidly Translocates through the Plasma Membrane and Accumulates in the Cell Nucleus", *J. Biol. Chem.*, 272(25):16010-16017 (1997).
Wang et al., "BID: a novel BH3 domain-only death agonist", *Genes Dev.*, 10:2859-2869 (1996).
Wang, X., "The Expanding Role of Mitochondria in Apoptosis", *Genes Dev.*, 15:2922-2933 (2001).
Wei et al., "Proapoptotic BAX and BAK: A Requisite Gateway to Mitochondrial Dysfunction and Death", *Science*, 292:727-730 (2001).
Wei et al., "tBID, a membrane-targeted death ligand, oligomerizes BAK to release cytochrome c", *Genes Dev.*, 14:2060-2071 (2000).
Weinstein, I.B., "Addiction to Oncogenes—the Achilles Heal of Cancer", *Science*, 297:63-64 (2002).
Willis et al., "Proapoptotic Bak is sequestered by Mcl-1 and Bcl-$x_L$, but not Bcl-2, until displaced by BH3-only proteins", *Genes Dev.*, 19:1294-1305 (2005).
Wolter et al., "Movement of Bax from the Cytosol to Mitochondria during Apoptosis", *J. Cell Biol.*, 139(5): 1281-1292 (1997).

(56) References Cited

OTHER PUBLICATIONS

Yamaguchi et al., "Bcl-XL Protects BimEL-induced Bax Conformational Change and Cytochrome c Release Independent of Interacting with Bax or BimEL", *J. Biol. Chem.*, 277(44):41604-41612 (2002).
Yang et al., "Bad, a Heterodimeric Partner for Bcl-$X_L$ and Bcl-2, Displaces Bax and Promotes Cell Death", *Cell*, 80(2):285-291 (1995).
Yasuda et al., "BNIP3α.: a Human Homolog of Mitochondrial Proapoptotic protein BNIP3", *Cancer Res.*, 59:533-537 (1999).
Zha et al.; "BH3 Domain of BAD is Required for Heterodimerization with BCL-$X_L$ and Pro-apoptotic Activity", *J. Biol. Chem.*, 272(39):24101-24104 (1997).
Zha et al., "Serine Phosphorylation of Death Agonist BAD in Response to Survival Factor Results in Binding to 14-3-3 Not BCL-$X_L$", *Cell*, 87:619-628 (1996).
Zong et al., "BH3-only proteins that bind pro-survival Bcl-2 family members fail to induce apoptosis in the absence of Bax and Bak", *Genes Dev.*, 15:1481-1486 (2001).
Polster et al., "BH3 Death Domain Peptide Induces Cell Type-selective Mitochondrial Outer Membrane Permeability," JBC, 2001, 276(41): 37887-37894.
Hans et al., "β-Carbolines induce apoptosis in cultured cerebellar granule neurons via the mitochondrial pathway," Neuropharmacology, 2005, 48:105-117.
Sugiyama Tomoyasu et al., "Activation of mirochondrial voltage-dependent anion channel by apro-apoptotic BH3-only protein Bim," Oncogene, vol. 21, No. 32, pp. 4944-4956, Jul. 25, 2002.
Degterev Alexei et al., "Identification of small-molecule inhibitors of interaction between the BH3 domain and Bcl-xl," Nature Cell Biology, vol. 3, No. 2, pp. 173-182, Feb. 2001.

\* cited by examiner

ASSAY SYSTEM TO IDENTIFY THERAPEUTIC AGENTS

RELATED APPLICATIONS

This application is a national stage application, filed under 35 U.S.C. §371, of International Application No. PCT/US2007/018238, filed on Aug. 16, 2007, which claims the benefit of U.S. Ser. No. 60/838,284 filed Aug. 16, 2006.

DESCRIPTION OF THE TEXT FILE SUBMITTED ELECTRONICALLY

The contents of the text file submitted electronically herewith are incorporated herein by reference in the entirety: A computer readable format copy of the Sequence Listing (filename: EUTR_004_01US_SeqList_ST25. txt, date recorded: Apr. 17, 2013, file size 3 kilobytes).

FIELD OF THE INVENTION

This invention relates generally to an assay system and methods for identifying modulators of apoptosis.

BACKGROUND OF THE INVENTION

The Bcl-2 (B cell lymphoma) family of proteins are genetically and functionally well characterized as being critical in effecting cellular apoptosis. Within this family are proteins that function either to protect cells against apoptotic signals or that induce apoptosis. A balance of interactions between the pro- and anti-apoptotic Bcl-2 family proteins determines whether the cell undergoes apoptosis or remains healthy. Bcl-2 is found to be over-expressed in many tumors including B-cell lymphomas, adenocarcinomas of the colon and prostate, gastric and naso-pharyngeal cancers. Bcl-2 has also been implicated in resistance of tumor cells to chemotoxic drugs or radiation. Over-expression of Bcl-2 in T cells causes their inappropriate resistance to apoptotic cues and subsequent likely auto-reactivity. Furthermore, expression levels of various members of the Bcl-2 family of proteins effects the onset and progression of these diseases. Therefore, Bcl-2 family of proteins represents important molecular targets for therapeutic intervention for many diseases.

Short peptide binding motifs, or domains (e.g. BH3 domains), in this family of proteins mediate many of the key interactions. These domains share structural features that can be exploited in identifying novel therapeutics that regulate these interactions. A key challenge for the drug industry is to discover small molecules or peptides that block domain-mediated protein-protein interactions, and do so in a subset specific manor. Thus, a need exists for an assay system that can efficiently identify compounds that that regulate (inhibit or enhance) BCL-2 mediated apoptosis.

SUMMARY OF THE INVENTION

The invention provides an assay system and methods for screening for inhibitors of the Bcl-2 family of proteins.

In various aspects the invention provides an assay system containing a liposome reagent and an immobilized BH3 domain peptide. In further aspects the invention provides an assay system containing mitochondria, an immobilized BH3 domain peptide and a mitochondrial binding agent, e.g. an anti-VDAC antibody. Mitochondria are isolated from a cell such as a cancer cell. Optionally, the mitochondria are labeled with a potentiometric dye such as JC-1 or dihydrorhodamine 123.

Preferably, the BH3 domain peptide and the mitochondrial binding agent are attached to a solid substrate. A solid substrate is for example a microarray or microparticles. Optionally, the solid substrate contains a control peptide such as a SH2 domain peptide.

By BH3 domain peptide is meant that the peptide contains the amphipathic a-helical domain from a protein belonging to the BCl-2 family. Proteins belonging to the BCL-2 family include for example Bcl-2, Bcl-$X_L$, Mcl-1, BAX, and BAK. The BH3 domain peptide is an activating peptide. An activating BH3 peptide is a peptide which activates BAX or BID to kill cells. Alternatively the BH3 domain peptide is a sensitizing peptide. A sensitizing BH3 peptide is a peptide which sensitizes a cell to apoptosis. Exemplary BH3 domain peptides include the amino acid sequences of SEQ NO 1-6 or 7.

A liposome reagent contains a liposome in which a BCL-2 family protein attached to said liposome and a detection reagent encapsulated within the liposome. The liposome is composed of vesicle forming lipids such as phosphatidyl choline, phosphatidyl serine, phosphatidyl inositol or cardiolipin. Optionally, the liposome contains at least 10 mole percent of cardiolipin. Additionally, the liposome contains at least 1 mole percent of vesicle forming lipid that is derivatized with 4,4-difluoro-3a,4a-diaza-s-indacene (BODIPY). The liposome contain 2, 3, 4, 5 or more mole percent of BODIPY.

A detection reagent is any reagent suitable to facilitate the identification or qualification of pore formation in the liposome. For example, the detection reagent is a fluorochrome, a chromogen or a dye. Exemplary detection reagents include fluorescein dextran or coumeran dextran.

Also included in the invention are methods of method of identifying an activating BH3 and sensitizing mimetic by contacting a test compound with a liposome assay system according to the invention and detecting binding of the liposome reagent to the solid substrate and release of the detection reagent from the liposome. A decrease in binding of the liposome reagent in the presence of the test compound compared to the absence of the test compound and release of the detection reagent indicates that the test compound is an activating BH3 mimetic. In contrast, a decrease in binding of the liposome reagent in the presence of the test compound compared to the absence of the test compound and no release of the detection reagent from the liposome indicates that the test compound is a sensitizing BH3 mimetic. Also provided by the invention are methods of predicting sensitivity of a cancer cell or subject to a therapeutic agent by contacting a mitochondria that has been isolated from a cancer cell from a subject and labeled with a potentiometric dye and a solid substrate containing and immobilized BH3 domain peptide and a mitochondrial binding agent under conditions where the mitochondria and mitochondrial binding agent are capable of forming a complex. The complex is contacted with a test therapeutic agent and the release of the potentiometric dye from the mitochondria is detected. Optionally, the complex is washed prior to contacting the complex with the test therapeutic agent or the complex is labeled prior to detecting potentiometric dye release. An increase in release of the potentiometric dye from the mitochondria in the presence of the test therapeutic agent compared to the absence of the test therapeutic agent indicates that the cancer cell or subject is sensitive to the therapeutic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1A:
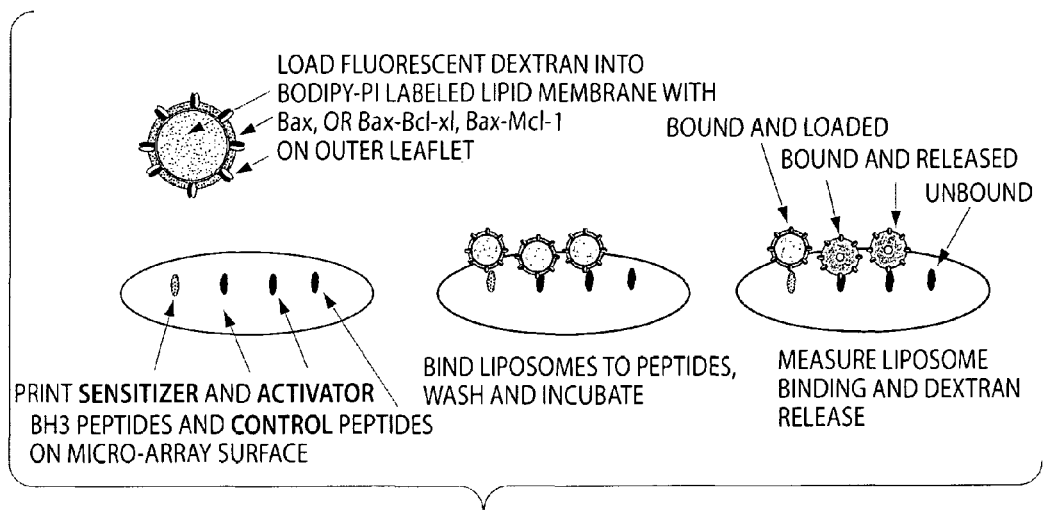
FIGS. 1A and 1B are schematics depicting a liposome binding and release assay.
Figure 1B:
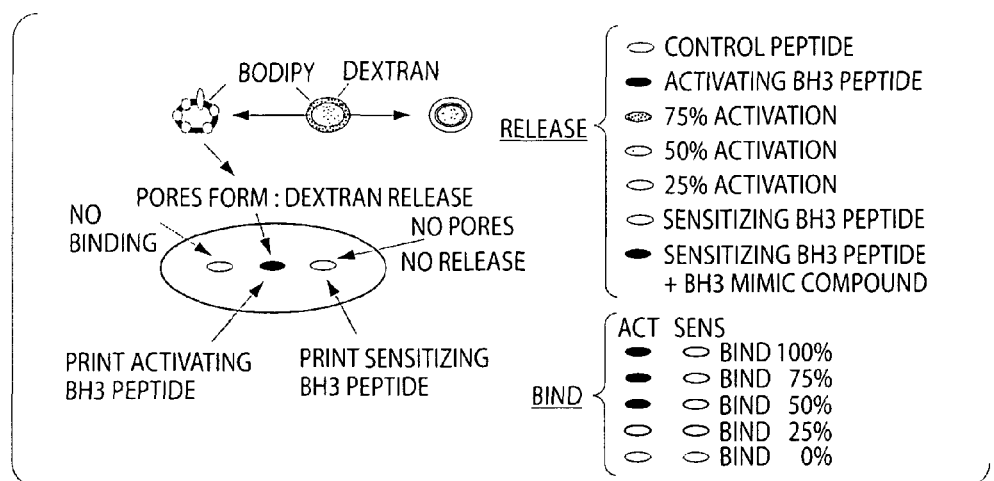
Figure 2:
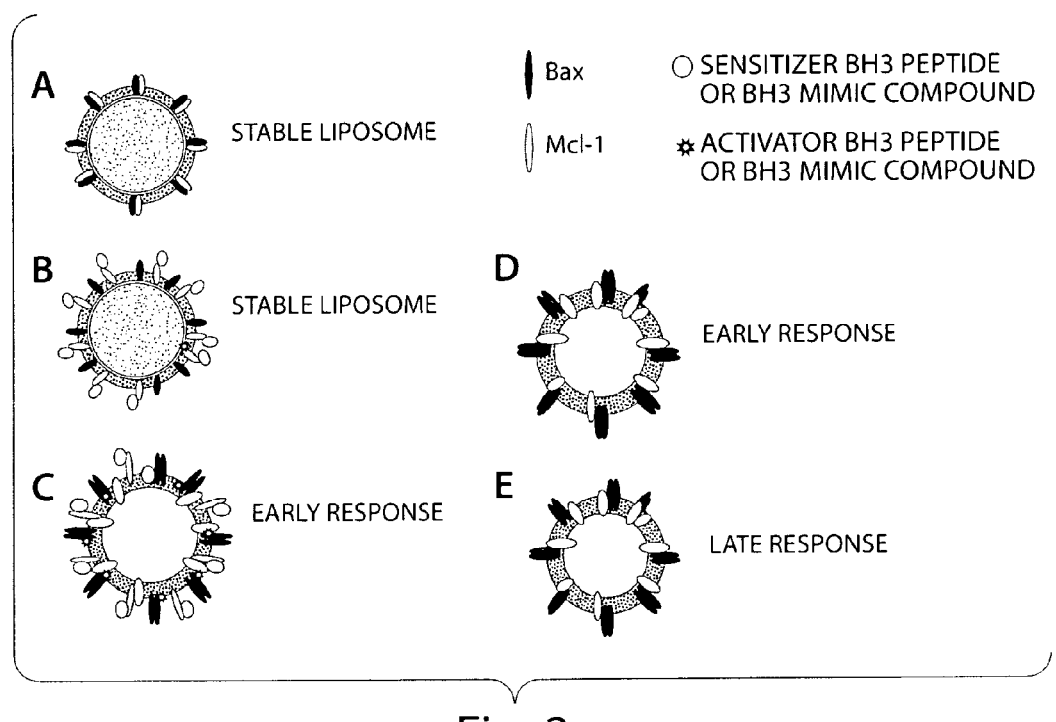
FIG. 2 is a schematic depicting a liposome release profile. Panel A shows a stable liposome having BAX and Mcl-1 paired in the membrane. Panel B shows binding of a sensitizer BH3 peptide or a BH3 mimic compound competing with Mcl-1/BAX binding. Panel C and D shows a BH3 activator inducing BAX oligomerization and the resulting pore formation. Panel E shows BAX oligomerization and the resulting pore formation in the absence of a BH3 only protein.
Figure 3:
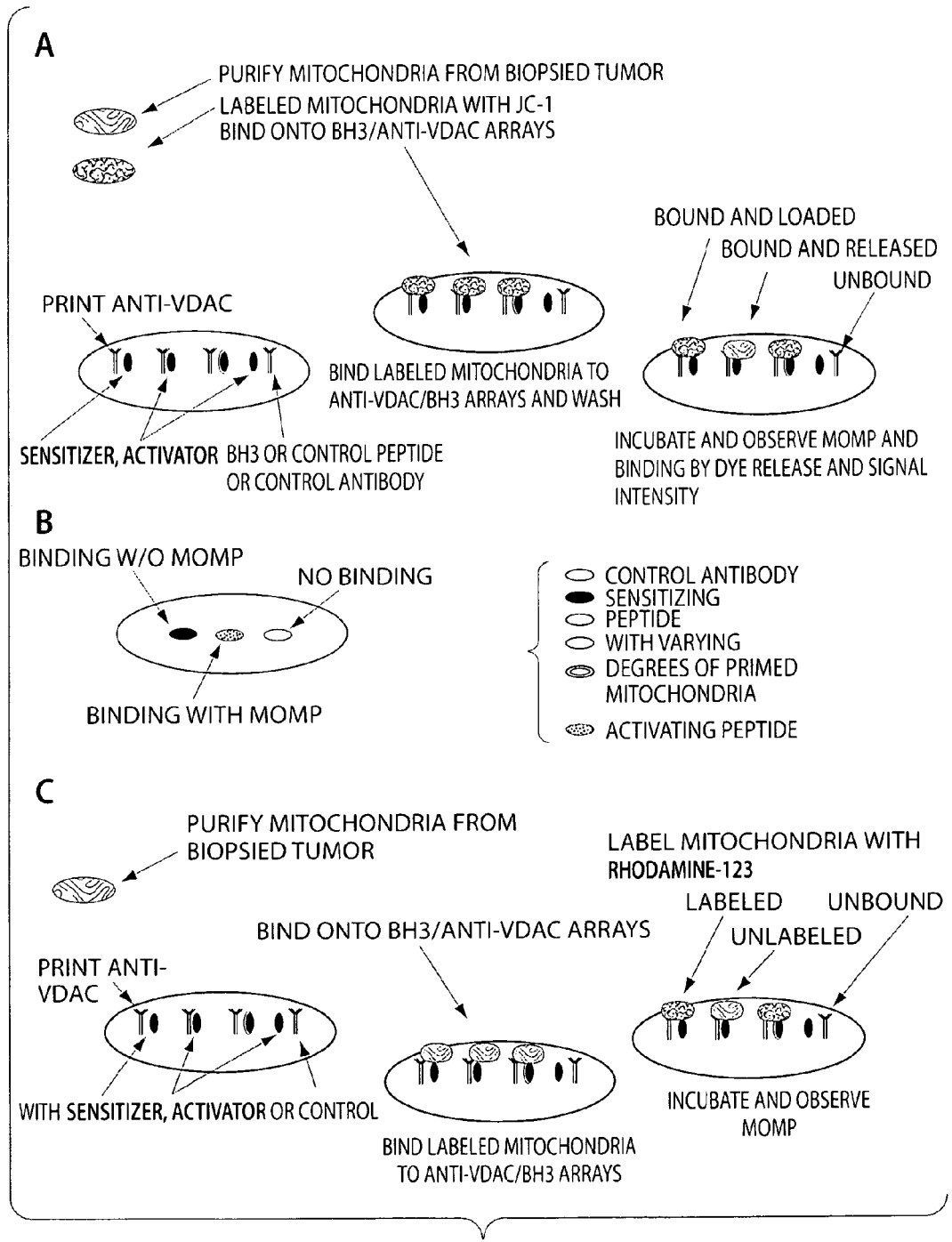
FIG. 3 is a schematic depicting a mitochondrial release profile. Panel A shows FIG. 3 purified mitochondria from a biopsied tumor is labeled with JC-1 and bound onto a BH3/anti-VDAC array. Panel B shows the three options for results: binding without MOMP, binding with MOMP, and no binding. Signal intensity correlates to an amount of MOMP and the degree of sensitivity of these mitochondria indicates a primed state. Panel C shows purified mitochondria from a biopsied tumor is bound onto a BH3/anti-VDAC array, as described in panel A, incubated for 10, 20, 30, or 60 minutes, and the bound mitochondria is detected by labeling with the potentiometric dye rhodamine 123 (Invitrogen Inc., Carlsbad, CA).

The invention provides an assay system for screening for inhibitors of protein-protein interactions. More specifically, the assay screens for inhibitors of the Bcl-2 family of proteins.

Proteins in the Bcl-2 family are major regulators of the commitment to programmed cell death as well as executioners of death signals at the mitochondrion. Members of this family include both pro- and anti-apoptotic proteins and share homology in up to four conserved regions termed BCL-2 homology (BH) 1-4 domains. The family can be divided into three main sub-classes. The anti-apoptotic proteins, which include Bcl-2, Bcl-$X_L$, Mcl-1 are all "multidomain," sharing homology throughout all four BH domains. The pro-apoptotic proteins can be further subdivided and include multidomain proteins, such as BAX and BAK, which possess sequence homology in BH 1-3 domains. The more distantly related "BH3-only" proteins such as BID, NOXA, PUMA, BIK, BIM and BAD are all pro-apoptotic and share sequence homology within the amphipathic α-helical BH3 region, which is required for their apoptotic function. The BH3-only proteins can be further subdivided into those that sensitize cells for apoptosis (BAD and NOXA) and those that activate BAX and BID to kill cells (BID, BIM and PUMA).

All of the Bcl-2 proteins function to effect intrinsic, or mitochondrial mediated, apopotosis. The BH3-only proteins have distinct roles in sensing different upstream apoptotic stimuli and integrating mitochondrial events. Thus, the BH3 domain is essential for apoptosis-effecting interactions among the Bcl-2 family of proteins. Specifically, binding of the anti-apoptotic proteins to multi-domain pro-apoptotic proteins blocks their apoptotic function by sequestering BH3 domains. The BH3-only proteins antagonize the anti-apoptotic function and promote pro-apoptotic protein function. Thus, the control of BH3-mediated binding is therefore important in regulating apoptosis or proliferation of cells. Identifying and developing small molecules that could inhibit or mimic these interactions is a promising area in developing therapeutics for treating many diseases, such as cancer or autoimmune disease. Moreover, small molecule screens that are able to select specific BH3 binding inhibitors will find molecules that modulate particular types of apoptosis and therefore be more specific and less toxic therapeutics.

According in one aspect the invention provides a two part assay system to screen for BH3 mimetics, e.g., either sensitizer mimetics or activator mimetics. The assay system allows for the simultaneous analysis of multiple protein binding events in a micro-array format. In addition to detecting binding events the assay further allows the detection of a functional event that is affected by the binding event. The assay system of the invention overcomes various problems currently encountered in the current approach in screening for protein interaction inhibitors such as, therapeutic targets are often many proteins with related function, allosteric effects are hard to determine, failure to qualify activity in conjunction with binding often causes spurious results, and protein targets often function in a lipid bilayer in a cell but not screens.

The assay system of the invention combines protein microarray binding assay to detect Bcl-2 family protein-protein interaction and a pore forming assay to detect membrane permeabilization. Central to intrinsic, i.e., mitochondria involved apoptosis is the migration of the pro-apoptotic protein BAX or BAK, to the outer membrane of the mitochondria (OMM). Following insertion into the OMM these proteins elicit the release of cytochrome c and other proteins that activate the caspases and promote apoptosis. Evidence indicates that the pro-apoptotic proteins form pores at the OMM similar to that of pore forming bacterial toxins, diptheria and colocin. Further, these proteins form pores when incorporated into purely lipid/phospholipid bi-layer membranes.

Currently, there are methods for incorporating purified Bax or Bak into synthetic liposomes and measuring their pore forming activity either alone or in combination with their biologically relevant binding partners. In contrast, the present invention extends the range of this functional pore-forming assay by coupling it to the BH3 domains array. This assay system will allow the evaluation of the effect of BH3 domain binding to Bax alone or together with Mcl-1 or Bcl-xL on pore formation. With this assay system the effects of BH3 mimic compounds on both particular BH3 mediated binding and particular BH3 effect on pore formation can be assessed simultaneously by using a multi-color readout as described herein.

Accordingly, in one aspect the invention provides an assay system that includes a liposome reagent and a peptide, e.g., BH3 domain peptides immobilized on solid substrate. In another aspect, the invention provides an assay system that includes an isolated mitochondria and a mitochondria binding agent and a BH3 domain peptides immobilized on solid support. A mitochondria binding agent is an agent that specifically binds to a mitochondria. For example a mitochondria binding agent is an antibody to a mitochondrial membrane protein such as Voltage-dependent anion-selective channel protein 1 (VDAC). Optionally, the mitochondria are labeled with a detection reagent such as a potentiometric dye. Potentiometric dyes include for example, 5,5',6,6'-tetrachloro-1,1',3,3'-tetraethyl-benzimidazolylcarbocyanine iodide (JC-1 iodide); 5,5',6,6'-tetrachloro-1,1',3,3'-tetraethyl-benzimidazolylcarbocyanine chloride (JC-1 chloride); tetrabromorhodamine 123, bromide; (2-(4-(dimethylamino)styryl)-N-ethylpyridinium iodide (DASPEI); dihydrorhodamine 123; 3,3'-dihexyloxacarbocyanine,iodide; nonyl acridine orange; tetramethylrhodamine ethyl ester, perchlorate and tetramethylrhodamine methyl ester, perchlorate Also include in the invention are method of screening for BH3 mimetics, predicting sensitivity of a cell to a therapeutic agent and selecting a therapeutic agent for a subject using the assay systems of the invention.

Liposome Reagents

A liposome reagent includes a liposome, a BCL-2 family protein or fragment thereof attached to the liposome; and a detection reagent encapsulated with the liposome Encapsulated as used herein with regard to the contents of the liposome describes materials that are within the interior aqueous volume of the liposome. Containing or attached as used herein describes materials that are intercalated in the lipid bilayer of the liposome, or partly intercalated in the lipid bilayer of the liposome.

The liposome is composed of a vesicle forming lipid. By vesicle forming lipid it is meant a lipid that can form spontaneously into bilayer vesicles in an aqueous medium.

A BCL-2 family protein or fragment thereof includes an anti-apoptotic protein, such as Bcl-2, Bcl-$X_L$, Mcl-1, or a pro-apoptotic proteins such as BAX and BAK. Optionally, the liposome contains both a anti-apoptotic protein and a pro-apoptotic protein. In various aspects, the liposome contains a plurality of BCL-2 proteins attached to the liposome.

A detection reagent is any substance used to facilitate identification and/or quantitation of a pore formation in the liposome. The detection reagent is present in an amount effective to permit detection and/or quantitation. Detection reagents are directly observed or measured or indirectly observed or measured. Detection reagents include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems. The detection reagent can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The detection reagent may also take the form of a chemical or biochemical, or an inert particle, including but not limited to colloidal gold, microspheres, quantum dots, or inorganic crystals such as nanocrystals or phosphors. Alternatively, the detection reagent s a combination of a detection moiety and an inert particle such as dextran. For example, the detection reagent is fluorescein dextran or coumeran dextran.

Liposomes are self-assembling structures comprising one or more lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment.

Liposomes can have a single lipid bilayer (unilamellar liposomes, "ULVs"), or multiple lipid bilayers (multilamellar liposomes, "MLVs" or "SPLVs"). Each bilayer surrounds, or encapsulates, an aqueous compartment. Given this encapsulation of aqueous volume within a protective barrier of lipid molecules, liposomes are able to sequester encapsulated molecules, e.g., a detection reagent such as a fluorochrome, a chromogen, a dye, an enzyme, or an enzyme substrate. The release of these molecules from the liposome can be monitored by loss of fluorescence in a purified population of liposomes.

Liposomes can have a variety of sizes, e.g., an average diameter as low as 25 nm or as high as 10,000 nm or more. Size is affected by a number of factors, e.g., lipid composition and method of preparation, well within the purview of ordinarily skilled artisans to determine and account for, and is determined by a number of techniques, such as quasi-elastic light scattering, also within the artisans' purview.

Various methodologies, also well within the purview of ordinarily skilled artisans, such as sonication, homogenization, French Press application and milling can be used to prepare liposomes of a smaller size from larger liposomes. Extrusion (see, e.g., U.S. Pat. No. 5,008,050) can be used to size reduce liposomes, that is to produce liposomes having a predetermined mean size by forcing the liposomes, under pressure, through filter pores of a defined, selected size. Tangential flow filtration (WO89/008846), can also be used to regularize the size of liposomes, that is, to produce a population of liposomes having less size heterogeneity, and a more homogeneous, defined size distribution. The contents of these documents are incorporated herein by reference.

Liposomes of this invention can be unilamellar, or oligolamellar, and can have a size equal to that of liposomes produced by any of the methods set forth hereinabove. However, in preferred embodiments of this invention, the liposomes are unilamellar liposomes having number average sizes of about 50 to 500 nm. Preferably, the liposome is 250 nm.

Liposomes are composed of a variety of lipids, both amphipathic and nonamphipathic, obtained from a variety of sources, both natural and synthetic. Suitable liposomal lipids include, without limitation, phospholipids such as phosphatidylcholines ("PC's"), phosphatidylethanolamines ("PE's"), phosphatidylserines ("PS's"), phosphatidylglycerols ("PG's"), phosphatidylinositols ("PI's") and phosphatidic acids ("PA's"). Such phospholipids generally have two acyl chains, these being either both saturated, both unsaturated or one saturated and one unsaturated; said chains include, without limitation: myristate, palmitate, stearate, oleate, linoleate, linolenate, arachidate, arachidonate, behenate and lignocerate chains. Optionally, the liposome comprise mixtures of phospholipids Phospholipids can also be derivatized, by the attachment thereto of a suitable reactive group. For example, the phospholipid if derivatized with a lipophilic fluorophore such as 4,4-difluoro-3a,4a-diaza-s-indacene (BODIPY). Such derivation allows measurement of pore forming activity.

The liposomes may also, but are not required to, comprise additional lipids as well, said additional lipids being incorporated into the liposomes for a number of reasons apparent to artisans of ordinary skill in the field of liposomology. Such reasons, include, without limitation, stabilizing or targeting the liposomes, as well as further altering the liposomes' pharmacokinetic behavior. Suitable additional lipids include any of those lipids commonly recognized as suitable for incorporation in liposomes, including, without limitation, phospholipids, glycolipids and sterols. Preferably, the additional lipid includes cardiolipin.

Most preferably, liposomes of this invention have a lipid component which comprises a derivatized lipid and an additional lipid. Suitable liposomes and the methods of preparing them are described in U.S. patent application Ser. No. 08/951,056, incorporated herein in its entirety by reference.

The liposomal lipid can also comprise a "headgroup-modified lipid," i.e., a lipid having a polar group derivatized by the attachment thereto of a moiety capable of inhibiting the binding of serum proteins to a liposome incorporating the lipid. Incorporation of headgroup-modified lipids into liposomes thus alters their pharmacokinetic behavior, such that the liposomes remain in the circulation of an animal for a longer period of time then would otherwise be the case (see, e.g., Blume et al., 1993; Gabizon et al., 1993; Park et al., 1992; Woodle et al., U.S. Pat. No. 5,013,556; Allen et al., U.S. Pat. Nos. 4,837,028 and 4,920,016; the contents of these documents being incorporated herein by reference).

The liposome of this invention may be dehydrated, stored and then reconstituted such that a substantial portion of their internal contents are retained. Liposomal dehydration generally requires use of a hydrophilic drying protectant such as a disaccharide sugar at both the inside and outside surfaces of the liposomes' bilayers (see U.S. Pat. No. 4,880,635, the contents of which are incorporated herein by reference). This hydrophilic compound is generally believed to prevent the rearrangement of the lipids in liposomes, so that their size and contents are maintained during the drying procedure, and through subsequent rehydration. Appropriate qualities for such drying protectants are that they be strong hydrogen bond acceptors, and possess stereochemical features that preserve the intermolecular spacing of the liposome bilayer components. Alternatively, the drying protectant can be omitted if the liposome preparation is not frozen prior to dehydration, and sufficient water remains in the preparation subsequent to dehydration.

BH3 Domain Peptides

A BH3 domain contains the amphipathic α-helical BH3 domain from the Bcl-2 family proteins, BID, BIM. PUMA, BAD, NOXA, BAK and mule. No particular length is implied by the term "peptide". A BH3 domain peptide is less than 195 amino acids in length, e.g., less than or equal to 150, 100, 75, 50, 35, 25 or 15 amino acid in length. For example a BH3 peptide includes the sequence of SEQ ID NO: 1-7 shown in Table 1. The peptide induces BAK oligomerization and cytochrome c mobilization (e.g., release) from the mitochondria.

TABLE 1

| Bim BH3 | GGGIAQELRRIGDEFNAY | SEQ ID NO: 1 |
|---|---|---|
| Bid BH3 | GGGIARHLAQVGDSMDRS | SEQ ID NO: 2 |
| Bad BH3 | GGGYGRELRRMSDEFVDSF | SEQ ID NO: 3 |
| Puma BH3 | GGGEEQWAREIGAQLRRMALQNAQYERR | SEQ ID NO: 4 |
| Noxa BH3 | GGGPAELEVECATQLRRFGDLLNFRQ | SEQ ID NO: 5 |
| Bak BH3 | GGGQVGRQLAIIGDDINR | SEQ ID NO: 6 |
| MuleBH3 | GGGMTQEVGQLLQGMGDDVYQQYRSL | SEQ ID NO: 7 |

The BH3 domain peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Optionally, the BH3 domain peptide is a stapled peptide. Stapled peptides are chemically braced or "stapled" peptides so that their shape, and therefore their activity, is restored and/or maintained. In addition, stapled peptides are more resistant to degradation. Alternatively, the BH3 domain peptides are cyclic peptides. Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., Endocrinology, 137: 5182-5185 (1996)), or between two amino acid side chains. See, e.g., DeGrado, Adv Protein Chem, 39: 51-124 (1988).

BH3 domain peptides are operatively (e.g., covalently) linked to a non-BH3 peptide to form a chimeric protein. A non-BH3 peptide refers to a polypeptide having an amino acid sequence corresponding to a protein that is not substantially homologous to the BH3 peptide. The non-BH3 peptide allows the addition of a functionality to the BH3 domain peptide. For example the non-BH3 peptide is a translocation sequence, a GST protein or a portion of an immunoglobulin molecule, e.g. the Fc region.

BH3 domain peptides are easily prepared using modern cloning techniques, or may be synthesized by solid state methods or by site-directed mutagenesis. A domain BH3 peptide may include dominant negative forms of a polypeptide. In one embodiment, native BH3 domain peptides can be isolated from cells or tissue sources by an appropriate purification scheme using standard protein purification techniques. In another embodiment, BH3 domain polypeptides are produced by recombinant DNA techniques. Alternative to recombinant expression, BH3 domain peptides can be synthesized chemically using standard peptide synthesis techniques.

An "isolated" or "purified" protein or biologically active portion thereof is substantially free of cellular material or other contaminating proteins from the cell or tissue source from which the BH3 domain peptide is derived, or substantially free from chemical precursors or other chemicals when chemically synthesized. The language "substantially free of cellular material" includes preparations of BH3 peptides in which the protein is separated from cellular components of the cells from which it is isolated or recombinantly produced. In one embodiment, the language "substantially free of cellular material" includes preparations of BH3 domain peptides having less than about 30% (by dry weight) of non-BH3 domain peptide a (also referred to herein as a "contaminating protein"), more preferably less than about 20% of non-BH3 peptide and/or non-transduction domain peptides, still more preferably less than about 10% of non-BH3 peptide, and most preferably less than about 5% non-BH3 domain peptide and/or non-transduction domain peptides. When the BH3 domain peptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BH3 domain peptides in which the protein is separated from chemical precursors or other chemicals that are involved in the synthesis of the protein. In one embodiment, the language "substantially free of chemical precursors or other chemicals" includes preparations of BH3 domain peptides having less than about 30% (by dry weight) of chemical precursors or non-BH3 domain peptide and/or non-transduction domain peptides chemicals, more preferably less than about 20% chemical precursors or non-BH3 domain peptide and/or non-transduction domain peptides chemicals, still more preferably less than about 10% chemical precursors or non-BH3 domain peptide chemicals, and most preferably less than about 5% chemical precursors or non-BH3 domain peptide and/or non-transduction domain peptides chemicals.

The term "biologically equivalent" is intended to mean that the compositions of the present invention are capable of demonstrating some or all of the same apoptosis modulating effects, i.e., release of cytochrome C or BAK oligomerization although not necessarily to the same degree as the BH3 domain polypeptide deduced from sequences identified from cDNA libraries of human, rat or mouse origin or produced from recombinant expression symptoms.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BH3 domain peptides can also include derivatives of BH3 domain peptides which are intended to include hybrid and modified forms of BH3 domain peptides including fusion proteins and BH3 domain peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 domain peptides. By retaining the biological activity, it is meant that cell death is induced by the BH3 polypeptide, although not necessarily at the same level of potency as that of the naturally-occurring BH3 domain polypeptide identified for human or mouse and that can be produced, for example, recombinantly. The terms induced and stimulated are used interchangeably throughout the specification.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 domain polypeptide is replaced with another amino acid residue from the same side chain family. Alternatively, in another embodiment, mutations can be introduced randomly along all or part of a BH3 coding sequence, such as by saturation mutagenesis, and the resultant mutants can be screened to identify mutants that retain activity.

Also included within the meaning of substantially homologous is any BH3 domain peptide which may be isolated by virtue of cross-reactivity with antibodies to the BH3 domain peptide described herein or whose encoding nucleotide sequences including genomic DNA, mRNA or cDNA may be isolated through hybridization with the complementary sequence of genomic or subgenomic nucleotide sequences or cDNA of the BH3 domain peptides herein or fragments thereof.

Solid Supports

The BH3 domain peptide and/or a mitochondrial binding agent is immobilized on a solid support. For example, the BH3 domain peptides or the mitochondrial binding agents are printed on a microarray. As used herein, the term "microarray" refers to a solid surface comprising a plurality of addressed biological macromolecules (e.g., BH3 domain peptides and mitochondrial binding agent). Optionally, the location of each of the macromolecules in the microarray is known, so as to allow for identification of the samples following analysis.

Alternatively, the BH3 peptide and/or a mitochondrial binding agent is immobilized on a microsphere. "Microsphere" refers to a small particle that can be covalently attached or otherwise coupled to a specific BH3 peptides and/or a mitochondrial binding agent for use in the compositions and methods of the present invention. The terms microsphere, particle, microparticle, bead or microbead are used interchangeably and bear equivalent meanings.

"Microsphere set" refers to a plurality of microspheres that share a defining "unique sorting characteristic" that allows the microspheres to be identified as part of a set and distinguished from microspheres that comprise a different microsphere set. The "unique sorting characteristic" can be detected, for example, by a flow cytometer, and serves as the basis for distinguishing one microsphere set from another. An exemplary "unique sorting characteristic" is the size of the bead. If bead size is chosen as the unique sorting characteristic, all beads within a specific microsphere set should be relatively the same size and all beads not part of that specific microsphere set should be of a different size.

Optionally, microsphere sets may be labeled with differing proportions of two or more fluorescent dyes, allowing the emission wavelengths and fluorescence intensities to serve as the unique sorting characteristic. For instance, in EXAMPLE 7, BH3 domain peptides (sensitizing and activating) were each coupled to unique microsphere sets provided by the Luminex Corp. (Austin, Tex.). In developing distinguishable, unique microsphere sets, Luminex internally color-coded populations of beads by varying the proportions of two fluorescent dyes. In the case of fluorescently-labeled microsphere sets, for example, beads from one microsphere set can be sorted or separated from beads belonging to another set and quantified by a flow cytometer.

In some aspects the solid support contains a control peptide. Control peptides include for example SH2 domain peptides such as c-able and p85. Exemplary control peptides include GGGDG-pY-EEIGA (SEQ ID NO:8; Src P-Y SH2) or GGGDG-pY-ENPGA (SEQ ID NO:9; C-Abl P-Y SH2)

As used herein, the terms "solid support" or "support" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). The BH3 domain peptide is immobilized, e.g., attached to a solid support when it is associated with the solid support through a non-random chemical or physical interaction. The attachment is through a covalent bond. Alternatively the attachments need not be covalent or permanent. Optionally, the BH3 domain peptides are attached to a solid support through a "spacer molecule" or "linking group." Such spacer molecules are molecules that have a first portion that attaches to the BH3 domain peptide and a second portion that attaches to the solid support. Thus, when attached to the solid support, the spacer molecule separates the solid support and the BH3 domain peptide, but is attached to both.

Screening Methods

The invention further provides methods of screening for compounds that modulate apoptosis, i.e., activators and sensitizers and method of determining sensitivity of a cell to an agent.

Apoptosis modulator compounds are identified by contacting a liposome reagent having an encapsulated detection reagent and containing an anti-apoptotic protein, e.g. BCL-2 or BCL-$X_L$ and a pro-apoptotic protein, e,g, BAX of BAK with an immobilized BH3 domain peptide to form a liposome-peptide complex. The complex is contacted with a candidate compound. Liposome-peptide complex and detection reagent release is determined and compared to the liposome-peptide complex formation and detection reagent release in the test population to a control population that has or has not been exposed to the compound. A decrease in liposome-peptide complex formation and an increase in detection reagent release in the presence of the compound as compared to the absence of the compound indicates the compound is an apoptotic activator. Whereas, a decrease liposome-peptide complex formation and a decrease in detection release in the presence of the compound as compared to the absence of the compound indicates the compound is an apoptotic sensitizer.

Cell sensitivity is determined by contacting a mitochondria isolated from the cell with a solid substrate in which a BH3 domain peptide and a mitochondrial binding agent is immobilized under conditions where that mitochondria and the mitochondrial binding agent is capable of forming a complex. Optionally, the mitochondria is labeled with a potentiometric dye. The complex is contacted with a test agent and release of cytochrome c or the potentiometric dye is determined and compared to release of cytochrome c or potentiometric dye in control population that has or has not been exposed to the compound. An increase in cytochrome c or potentiometric dye release in the presence of the compound as compared to the absence of compound indicates cell is sensitive to the therapeutic agent.

The cell is a cancer cell or a cell that is suspected of being cancerous. The cell is from a subject known to or suspected of having cancer. The subject is preferably a mammal. The mammal is, e.g., a human, non-human primate, mouse, rat, dog, cat, horse, or cow. The subject has been previously diagnosed as having cancer, and possibly has already undergone treatment for cancer. Alternatively, the subject has not been previously diagnosed as having cancer.

The test agent is a therapeutic agent such as a chemotherapeutic agent. For example the agent is a mimetic of sensitizer BH3 domains or an antagonist of an anti-apoptotic protein.

The invention also includes an apoptosis modulator identified according to this screening method, and a pharmaceutical composition which includes the apoptosis modulator.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXAMPLES

Example 1

Two Color Vesicle Release Assay

A simplified cell free system is used to detect Bax pore forming function on a lipid bilayer. The liposome release assay measures both the release of the fluorescently labeled contents and the lipid itself so a ratio of signals from each label or a shift in FRET will give accurate measurement of pore forming activity. Both a ratio of signals from each label and a shift in FRET are tested.

To accomplish this assay, purified proteins are incubated with synthetic liposomes labeled with BODIPY (either Phosphotidyl Inositol or Di-oc) and containing entrapped fluorescien dextran or coumeran dextran. The enhancement of Bax pore forming activity by BH3 peptide or BH3 mimic compounds is assessed in a liquid phase assay. Both colors will be read as well as the FRET signal generated from energy transfer between the fluorescence in the lumen of the liposome (coumeran or fluorescence) and that on the inner leaflet of the liposome. Efficiency is determined as $E=1-F_D/F°_D$ where $F_D$ and FoD are fluorescence intensities of the donor (Coumaran) in the presence and absence of the acceptor (BODIPY 530/550 C12-HPC) respectively. The labeling of the lipid is optimized by conducting several of the above described tests in order to fine tune the amounts of label that will facilitate an informed result.

The assay is also used to assess the kinetics of release from the vesicle. Purified Bcl-xL or Mcl-1 protein will be added to Bax containing liposomes to block pore forming activity as described. This block is relieved by addition of sensitizing BH3 domain peptides, from Bad or Noxa. The release of dextran from the liposome is normalized to the amount of liposome present. A ratio of the two selected labels allow relative amount of release to total liposome per reaction.

Formation of Hybrid Protein Probes

Human Bcl-xL-GST (Glutathione-S-Transferase) fusion protein is expressed with deleted transmembrane regions and full length human Bax-GST is cloned into pGEX 4T-1. These constructs are transfected into BL21 strain. GST fusion proteins are purified from cell culture lysates after induction with isopropyl-1-thio-β-D-galactopyranoside and purified using Amersham Hitrap Glutathione column on the ACTA-FPLC (Amersham). Similarly, Intein-Mcl-1 fusion protein is generated in *E. coli*, purified using chitin beads and cleaved from Intein domain (New England Biolabs, Ipswitch, Mass.), which stays bound to the beads.

Large Unilaminar Vesicles

Large unilaminar vesicles (LUVs) are prepared as described in part by Kuwana et al Cell 2002 Nov. 1; 111(3): 331-42. Equimolar concentrations (60 M lipid concentration) of phosphatidyl choline, phosphatidyl serine, phosphatydyl Inositol and cardiolipin, (Avanti Polar Lipids) with 2 mol % (1.2 mM BODIPY-lipid are co-dissolved in chloroform/methanol (2:1). Organic solvents are removed by evaporation under an argon gas stream and incubated in a vacuum for 2 hours. The dried film is resuspended in 100 mM KCl, 10 mM HEPES, 0.1 mM EDTA, pH 7.0 buffer with fluorescien isothiocyanate-labeled dextrans (FDs) of 70 kDa (FD-70) (Sigma) at 1 M.

LUVs are formed by the method of Mayer et al. using 10 freeze/thaw cycles and extruded twice through polycarbonate membranes of 0.2 mM (Nucleopore; San Diego, Calif.). Untrapped FDs will be removed by gel filtration in Sephadex G-25 and Sephacryl S-500 HR columns, FRET reading details and efficiency is determined as $E=1-F_D/F°_D$ where $F_D$ and FoD are fluorescence intensities of the donor (Coumaran) in the presence and absence of the acceptor (BODIPY 530/550 C12-HPC) respectively.

Alternatively the labeling is conducted using calcien in a liquid phase only assay. Calcien signal is measured as a ratio of total signal. Fluorescence of carboxyfluorescein (C194, C1904) or calcein (C481) is >95% self-quenched at concentrations >100 mM. Concentrated solutions of these water-soluble dyes are encapsulated in liposomes, which are then separated from any remaining free dye by gel filtration. Upon addition of permeabilizing agent, dye release is accompanied by an increase in fluorescence (excitation/emission maxima ~490 nm/520 nm). Complete lysis of the liposomes with 0.1% Triton X-100 can be used to determine the assay endpoint. Calcein may be preferred over carboxyfluorescein because of higher net charge and lower pH sensitivity. Note that this assay will detect any process that causes leakage of aqueous contents, including fusion, lysis or permeabilization.

Example 2

Assessment of Binding of the Two Color Lipid Vesicles to Printed BH3 Peptide Array A peptide array format is used to assess the binding of Bax vesicles. These arrays are highly sensitive at detecting non-lipid associated Bcl-xL, Bcl-2 and Bax binding. Assays are prepared as described below, except that the format is changed to accommodate the traditional microscope slide. Using the microscope slide for a rough determination of a read out is sufficient for a first level experiment to identify that the system works. In a second level of experimentation, the format described above in Example 1 is used. Liposomes are prepared as described in Example 1, and incubated on the arrays and allowed to bind and incubated over a time course. Condition for optimal binding is determined by the liposome release profile and the readouts that indicate binding of molecules to the BH3 binding domains. Binding constants are calculated.

To generate the peptide arrays, peptides comprised of the BH3 domains from the proteins Bid, Bim, and Puma, Bad and Noxa Bak and mule, as well as control phospho-peptides comprised of the SH2 domains c-able and p85 are printed on epoxy silane and aldehyde slides available through Erie scientific. Spots are printed with 1 mL of 1 mM solution of peptide in water. Previous experiments established that binding of purified proteins saturated at this concentration. Each sample is printed in triplicate in a 6×8 grid (16 samples) to accommodate a 32 well format (False bottom wells are available from Grace-Bio labs located in Bend, Oreg. and are assembled. Printing is done using the PerkinElmer Biochip Arrayer, on a fee for service basis by PerkinElmer Life Sciences, Boston, Mass.

Example 3

Optimization of Liposome Binding to Printed BH3 Peptides

Liposomes are labeled with combination of label determined in Example 1 above, and are prepared as described above. Liposome binding buffer includes PBS with other liposome compatible buffers. A phase 2 buffer is used without detergent, and the buffer specified in Kuwana et al can be used.

The Kds are established with purified proteins as a starting point and it is estimated that the amount of protein incorporated into a liposome is a direct function of the nature of the protein being used, and generally will agree with the amounts of protein incorporated into liposome for pore forming assays known in the art. The molar concentration of protein likewise follows generally that used for pore forming assays as described previously in the art.

Enough lipid is prepared to provide sufficient liposomes for the BH3 domain binding array, and is therefore loosely dependent on the amount of candidate therapeutic agents being tested and the amount of the BH3 domain binding molecules on a given micro-array or arrays that is coupled to the pore formation assay.

Liposomal solutions are titrated in 96 well plates in a 4 fold serial dilution covering 2 uM to 0.1 nM series. 40 ul are transferred using a 8 position repeating pipetter onto the micro-arrays.

Liposomes are allowed to incubate for 30 minutes, 1 hour, 2 hours, or 4 hours at room temperature. Slides are washed gently. Wash conditions are established as generally optimal for the assay so that the liposomes remain on the slides. Slides are spun dry at room temperature and then read on an Axon array reader from Illumina located in San Diego, Calif. Individual spots with each 6×8 grid are analyzed for signal volume using Array Vision software located at Imaging Research, Inc. available from G.E. Healthcare, Inc. Binding constants Kd for each BH3 domain peptide or molecule (if non-protein molecules are tested) are derived from linear regression analysis performed using graphpad prism software (San Diego, Calif.).

In addition to simple binding, two color measurements determine the release of liposomal contents. Readings at 488 and 520 will be taken as well as 547 for FRET. Location of liposome signal in array grid coupled with shift of 488:520 ratio will indicate particular BH3 peptide activity in affecting Bax mediated pore formation, either directly, in Bax only liposomes, or by relieving Mcl-1 or Bcl-xL inhibition of pore formation.

For liposomes that contain both apoptotic and anti-apoptotic proteins the possible effects of these competing peptides or small molecules are:
1. liposomes are bound to the arrays by Bax binding, the consequence of which is pore formation if bound to activating BH3 peptide.
2. liposomes are bound by Bcl-xL or Mcl-1 and the BH3 peptides are displaced by sensitizing peptides or molecules, the consequence of which is release of pore forming inhibition and induction of pore formation. These activities are related to Kd of the binding of the test therapeutic. Results are charted for each candidate competing against each BH3 domain protein.

Example 4

Assess Affect of Soluble BH3 Peptides or BH3 Mimic Compounds on Liposomes Bound to BH3 Array After the optimal binding and optimal release conditions are established the soluble reagents are treated with BH3 peptides or other molecules that effect binding and release of color or dye from the liposome. Liposomes that contain both apoptotic and anti-apoptotic proteins captured on arrays by BH3 peptides will either:
1. Release of dye with the addition of the peptide or compound
2. Remain bound and release the dextran following pore formation
3. Remain bound and have no pores form, or have Bax activity blocked
4. Be released and have pores form.

Figure 4:
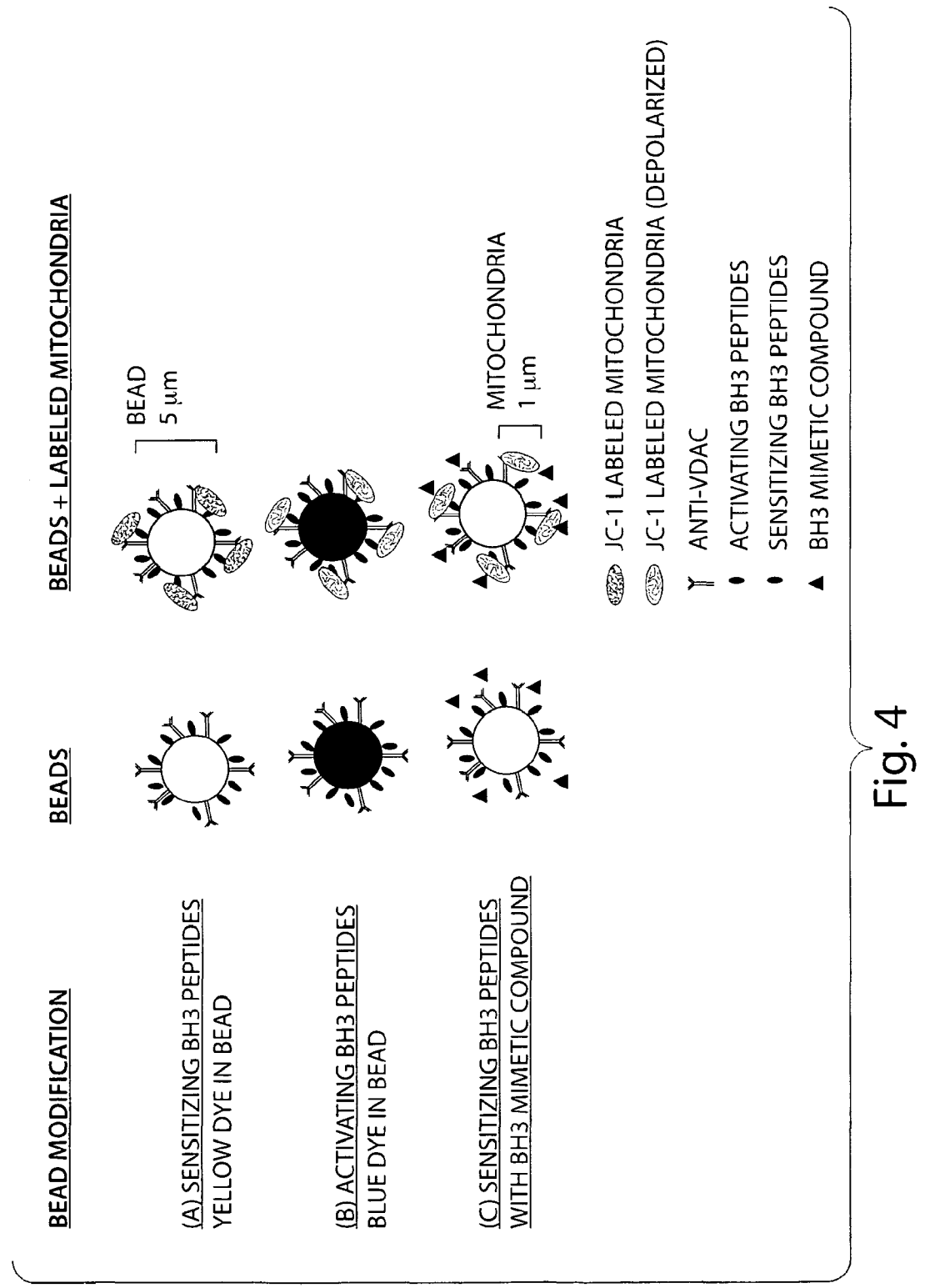
FIG. 4 is a schematic depicting a mitochondrial BH3 response profile using modified Luminex beads:. Purified Mitochondria are loaded with JC-1. Luminex beads are derivatized with anti-VDAC antibody and one of the either sensitizing BH3 peptides without (A) or with (C) BH3 mimetic compounds, or activating BH3 peptides (B). Each peptide is distinguished by a particular bead color. Shift in JC-1 emission from red (590 nM) to green (527 nM) indicates loss of membrane potential. Multiple interactions are read within single reactions.

Accordingly, with the establishment of the above described assay systems, the various activities of BH3 peptides will be assembled. The pore forming effects are distinguished from the competitive binding activity. FIG. 4 indicates pore forming activity on bound liposomes (EC50) of BH3 peptides A chart is assembled indicating competing activity of all BH3 peptide on binding of liposomes and release of contents (pore formation). For example, it is expected that a Bax-Mcl-1 liposome binding to Noxa would displace dye from the liposome, and although a Bim mimic is expected to bind, it is not expected to cause release of dye from the liposome. I Example 5

Profile Response of Anti-VDAC Captured Mitochondria to Arrayed BH3 Peptides

Mitochondria from healthy tissue, tumor progenitor, or tumor cells is characterized by their state of responsiveness to certain BH3 mediated signals. As described by Letai et al, J Clin Invest. 2005 October; 115(10):2648-55 and others, mitochondria in a BH3 primed state respond more quickly to certain apoptotic cues, especially BH3 mediated cues. Profiling the response of purified mitochondria to BH3 peptides has been proposed as a means to assess likelihood of certain tumor cells to respond to certain therapy. This example demonstrates a method to profile purified mitochondria for such sensitivity and thereby qualify their tissue of origin for treatment.

Binding and release assay; Mitochondria are partially purified from circulating PBCs or from cells collected from biopsied tumor samples by cell fractionation as described in Methods Enzymol. 2000; 322:235-42 and Cancer Cell 2004; Cell 2, 183-192. Cells are suspended in cold hypotonic lysis buffer, 259 mM sucrose, 10 mM Tris-Hcl pH(7.4), 1 mM EGTA, and homogenized in a dounce rotary Teflon pestle followed by 6-10 expulsions through a 27-gauge needle. The mitochondrial cell fraction is separated from the heavy membranes by differential centrifugation. The resulting mitochondrial fraction is resuspended to a final protein cincentration of 5 mg/ml in assay binding buffer consisting of, 125 mM KCL, 10 mM Tris-HCl (pH 7.4), 0.1 mM EGTA, pH 7.2, 20 µM ATP. Mitochondria are then labeled the dye JC-19 (Invitrogen)

The green-fluorescent JC-1 probe (5,5',6,6'-tetrachloro-1, 1',3,3'-tetraethylbenzimidazolylcarbocyanine iodide) is a lipophilic, cationic dye that enters mitochondria in proportion to the membrane potential JC-1 exists as a monomer in water at low membrane potential (M). However, at higher potentials, JC-1 forms red-fluorescent "J-aggregates". As a monomer the dye has an absorption/emission maxima of 527 nm while at high membrane potential the emission maximum is 590 nm. Thus, ratio measurements of the emission of this cyanine dye can be used as a sensitive measure of mitochondrial membrane potential. The dye allows for a dual measurement of dye concentration that does not require the measurement of a nuclear or cytoplasmic reference values. Studies using isolated mitochondria have shown that the 527 nm emission from monomeric JC-1 increases almost linearly with membrane M potentials ranging from 46 to 182 mV, whereas the 590 nm J-aggregate emission is less sensitive to M values less negative than 140 my and is strongly sensitive to potential values in the range of 140 to 182 mV (Di Lisa et al., 1995) Optical filters designed for fluorescein and tetramethylrhodamine can be used to separately visualize the monomer and J-aggregate forms, respectively. Alternatively, both forms can be observed simultaneously using a standard fluorescein longpass optical filter set. Before each experiment, mitochondria at 5 mg/ml will be incubated with JC-1(10 ug/ml) in binding buffer for 5 min in the dark.

Array surfaces are prepared with an antibody against the human-VDAC-1 that binds to the outer mitochondrial membrane loop, for instance, residues 185-197, (Biodesign Internqtional)/Meridian Life Sciences, Saco Mass.) printed onto reactive glass surfaces (aldehyde or silane epoxy slides commercially available from Erie Scientific, (Portsmouth, N.H.), or derivatized onto color coded beads, such as those provided by Luminex corporation, (Austin, Tex.), along with the BH3 peptides described above in a 1:4 or 1:10 (antibody:peptide) molar ratio using commercially available micro-array printers. The reactive surfaces of the printed arrays are quenched and blocked according to the manufacturers specifications, rinsed and stored as described above.

Mitochondria are allowed to incubate onto the arrays for 10, 20, 40, or 60 minutes at room temperature and then washed 3× with PBS containing ATP at 10 uM. One A positive control for complete loss of membrane potential(M) is the addition of 300 µM $CaCl_2$. The negative control will be untreated samples or samples treated with random or inactive mutant BH3 peptides known to be inactive Hockenberry reference describing this sequence.

Slides are spun dry and read using the Axon reader at 527 and 590.

The emission signals at 590 and 527 nm elicited by excitation at 485 nm will be measured following 3 wash cycles for 2 minutes with binding buffer. The ratio of the signal at 590 nm over that at 527 nm (red:green ratio) was calculated to estimate □□M.

In an alternative approach unlabeled mitochondria will be incubated onto the BH3 slides as described above. Following incubation periods of 10, 20 30 or 60 minutes the potentiometric dye rhodamine 123 (Invitrogen Inc. Carlsbad, Calif.) will added at 20 nM final concetration in 100 mM KCl, 10 mM potassium phosphate buffer 10 mM Tris-HCl(pH 7.4), 10 mM $MgCl_2$, 5 mM pyruvate, 2.5 mM malate for a total of 5 minutes as described in The Journal of Neuroscience, Sep. 15, 2004•24(37):8019-8028. Surfaces will be washed three times and read on the reader set for excitation of 488 nm and emission of 529 nm.

This labeling protocol will selectively label mitochondria that maintain membrane potential following exposure to BH3 peptides allowing determination of loss of M.

Example 6

Profile Response Poteiometric Dye Labeled Mitochondria to Soluble BH3 Peptides in Microwells Mitochondria from healthy tissue, tumor progenitor, or tumor cells are prepared as described above and labeled with the JC-1 dye before exposure, or rhodamine after exposure to BH3 peptides or BH3 mimic compounds as described above.

Mitochondrial response, loss of M, is measured in 384 well plates using a standard fluorescent plate reader. Reaction volumes are 15 µl per well. BH3 peptides are titrated into the reaction volumes in a dilution series and allowed to incubate over a time course that will range from 1 to 60 minutes.

Example 7

Profile Response Potentiometric Dye Labeled Mitochondria to Soluble BH3 Peptides Using Color-Coded Micro-Beads as Sold Substrate Micro-beads of 5 micron diameter and color coded (Luminex Incorporated) are derivatized with BH3 peptides and the Anti-human VDAC-1 recognizing the outer mitochondrial residues. Each different BH3 domain peptide will be derivatized to a different colored Luminex bead. Antibodies recognizing the outer mitochondrial membrane portions of the Human mono-amine oxideas A, or mono-amine oxidase B can also be used to anchor the mitochondria to the sold substrate.

Mitochondria from healthy tissue, tumor progenitor, or tumor sells are prepared as described above and labeled with the JC-1 dye before exposure, or rhodamine after exposure to BH3 peptides or BH3 mimic compounds as described above (FIG. 4). Altered emission spectra will indicate loss of membrane potential. Response of mitochondria bound to each of the different BH3 derivatized beads will be decoded.

What is claimed is:

1. An assay system comprising:
   a) an isolated mitochondria; and
   b) a solid substrate comprising:
      i) an immobilized BH3 domain peptide of less than 195 amino acids and
      ii) an immobilized anti-VDAC antibody.

2. The assay system of claim 1, wherein said mitochondria is isolated from a cancer cell.

3. The assay system of claim 1, wherein said mitochondria is labeled with a potentiometric dye.

4. The assay system of claim 3, wherein said potentiometric dye is JC-1 or dihydrorhodamine 123.

5. The assay system of claim 1, wherein said BH3 domain peptide is an activating BH3 peptide.

6. The assay system of claim 1, wherein said BH3 domain peptide is a sensitizing BH3 peptide.

7. The assay system of claim 1, wherein said BH3 domain peptide comprises an amino acid sequence selected from SEQ ID NO: 1-7.

8. The assay system of claim 1, wherein said solid substrate is a microarray or a microsphere.

* * * * *

SEQUENCE LISTING

```
<160> NUMBER OF SEQ ID NOS: 9

<210> SEQ ID NO 1
<211> LENGTH: 18
<212> TYPE: PRT
<213> ORGANISM: Homo sapiens

<400> SEQUENCE: 1

Gly Gly Gly Ile Ala Gln Glu Leu Arg Arg Ile Gly Asp Glu Phe Asn
1               5                   10                  15

Ala Tyr

<210> SEQ ID NO 2
<211> LENGTH: 18
<212> TYPE: PRT
<213> ORGANISM: Homo sapiens

<400> SEQUENCE: 2

Gly Gly Gly Ile Ala Arg His Leu Ala Gln Val Gly Asp Ser Met Asp
1               5                   10                  15

Arg Ser

<210> SEQ ID NO 3
<211> LENGTH: 19
<212> TYPE: PRT
<213> ORGANISM: Homo sapiens

<400> SEQUENCE: 3

Gly Gly Gly Tyr Gly Arg Glu Leu Arg Arg Met Ser Asp Glu Phe Val
1               5                   10                  15

Asp Ser Phe
```

```
<210> SEQ ID NO 4
<211> LENGTH: 28
<212> TYPE: PRT
<213> ORGANISM: Homo sapiens

<400> SEQUENCE: 4

Gly Gly Gly Glu Glu Gln Trp Ala Arg Glu Ile Gly Ala Gln Leu Arg
1               5                   10                  15

Arg Met Ala Leu Gln Asn Ala Gln Tyr Glu Arg Arg
            20                  25

<210> SEQ ID NO 5
<211> LENGTH: 26
<212> TYPE: PRT
<213> ORGANISM: Homo sapiens

<400> SEQUENCE: 5

Gly Gly Gly Pro Ala Glu Leu Glu Val Glu Cys Ala Thr Gln Leu Arg
1               5                   10                  15

Arg Phe Gly Asp Leu Leu Asn Phe Arg Gln
            20                  25

<210> SEQ ID NO 6
<211> LENGTH: 18
<212> TYPE: PRT
<213> ORGANISM: Homo sapiens

<400> SEQUENCE: 6

Gly Gly Gly Gln Val Gly Arg Gln Leu Ala Ile Ile Gly Asp Asp Ile
1               5                   10                  15

Asn Arg

<210> SEQ ID NO 7
<211> LENGTH: 26
<212> TYPE: PRT
<213> ORGANISM: Homo sapiens

<400> SEQUENCE: 7

Gly Gly Gly Met Thr Gln Glu Val Gly Gln Leu Leu Gln Gly Met Gly
1               5                   10                  15

Asp Asp Val Tyr Gln Gln Tyr Arg Ser Leu
            20                  25

<210> SEQ ID NO 8
<211> LENGTH: 11
<212> TYPE: PRT
<213> ORGANISM: Artificial Sequence
<220> FEATURE:
<223> OTHER INFORMATION: Src P-Y SH2 control peptide
<220> FEATURE:
<221> NAME/KEY: MISC_FEATURE
<222> LOCATION: (6)..(6)
<223> OTHER INFORMATION: Tyr may be phosphorylated

<400> SEQUENCE: 8

Gly Gly Gly Asp Gly Tyr Glu Glu Ile Gly Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: C-Abl P-Y SH2
<220> FEATURE:
```

```
<221> NAME/KEY: MISC_FEATURE
<222> LOCATION: (6)..(6)
<223> OTHER INFORMATION: Tyr may be phosphorylated

<400> SEQUENCE: 9

Gly Gly Gly Asp Gly Tyr Glu Asn Pro Gly Ala
1               5                   10
```